(12) United States Patent
Belzer et al.

(10) Patent No.: US 6,680,384 B2
(45) Date of Patent: Jan. 20, 2004

(54) PROCESS FOR PREPARING 4,6-DIAMINOPYRIMIDO[5,4-D]PYRIMIDINES

(75) Inventors: Werner Belzer, St. Goar (DE); Ralf Lock, Mainz (DE); Werner Rall, Mittelbiberach (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 10/095,926

(22) Filed: Mar. 12, 2002

(65) Prior Publication Data

US 2002/0198380 A1 Dec. 26, 2002

Related U.S. Application Data

(60) Provisional application No. 60/289,879, filed on May 9, 2001.

(30) Foreign Application Priority Data

Mar. 30, 2001 (DE) .......................................... 101 15 921

(51) Int. Cl.[7] .......................................... C07D 487/04
(52) U.S. Cl. ........................................ 544/256
(58) Field of Search ........................................ 544/256

(56) References Cited

U.S. PATENT DOCUMENTS 5,707,989 A   1/1998  Himmelsbach et al. .. 514/228.2
5,821,240 A   10/1998 Himmelsbach et al. ..... 514/212

FOREIGN PATENT DOCUMENTS

WO   WO 97 32880 A1   9/1997

OTHER PUBLICATIONS

Rewcastle, G. W. et al; "Tyrosine Kinase Inhibitors. 12. Synthesis and Structure–Activity Relationships for 6–Substituted 4–(Phenylamino)pyrimido[5,4–d]pyrimidines Designed as Inhibitors of the Epidermal Growth Factor Receptor"; J. Med. Chem. 1997, 40, pp. 1820–1826.

*Primary Examiner*—John M Ford
(74) *Attorney, Agent, or Firm*—Robert P. Raymond; Michael P. Morris; Alan R. Stempel

(57) ABSTRACT

The present invention relates to a process for preparing 4,6-diaminopyrimido[5,4-d]pyrimidines of formula I,

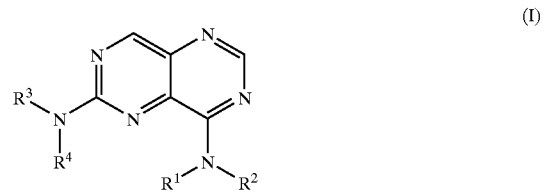

(I)

wherein $R^1$ to $R^4$ have the meanings given in claim 1, as well as new intermediate products which are involved in this process.

9 Claims, No Drawings

PROCESS FOR PREPARING 4,6-DIAMINOPYRIMIDO[5,4-D]PYRIMIDINES

RELATED APPLICATIONS

Benefit of U.S. Provisional Application Ser. No. 60/289,879, filed on May 9, 2001, is hereby claimed.

FIELD OF THE INVENTION

The invention relates to a process for preparing 4,6-diaminopyrimido[5,4-d]pyrimidines of formula I,

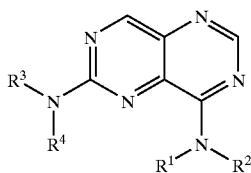

(I)

wherein $R^1$, $R^2$, $R^3$, and $R^4$ are defined as specified, from a compound of formula II,

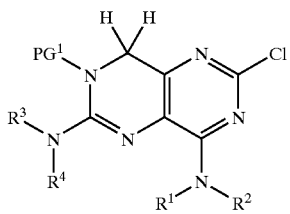

(II)

wherein $R^1$, $R^2$, $R^3$, and $R^4$ are defined as specified and $PG^1$ denotes a suitable protecting group.

BACKGROUND TO THE INVENTION 4,6-diaminopyrimido[5,4-d]pyrimidines are known for example from WO 97/32880 and are valuable pharmaceutical compositions which have, in particular, an inhibitory effect on signal transduction mediated by tyrosine kinases.

However, the method of preparation described therein is unsuitable for production on an industrial scale as the desired products are described as being obtained from starting materials which are not easily accessible, such as 4-anilino-6-methylsulphinyl-pyrimido[5,4-d]pyrimidines or 4-anilino-6-methylsulphonylpyrimido[5,4-d]pyrimidines which, when reacted, give off foul-smelling and toxic thiols which lead to contamination of the products.

The aim of the present invention is therefore to provide a process which makes it possible to synthesise, work up, purify and isolate 4,6-diaminopyrimido[5,4-d]pyrimidines of formula I on an industrial scale while overcoming the disadvantages mentioned above.

DETAILED DESCRIPTION OF THE INVENTION

Surprisingly, it has been found that 4,6-diaminopyrimido[5,4-d]pyrimidines of formula I
wherein
  $R^1$ denotes a hydrogen atom or a $C_1$–$C_6$ alkyl group,
  $R^2$ denotes an optionally substituted $C_6$–$C_{10}$ aryl group,
  $R^3$ denotes a hydrogen atom or a $C_1$–$C_6$ alkyl group, and
  $R^4$ denotes a hydrogen atom or an optionally substituted $C_1$–$C_6$ alkyl, $C_3$–$C_6$ alkenyl, $C_3$–$C_8$ cycloalkyl or a 4- to 7-membered, nitrogen-containing heterocyclyl group, or
  $R^3$ and $R^4$ together with the nitrogen atom linked to them denote an optionally substituted heterocyclyl group, can be prepared in high yields and in a comparatively small number of steps, if the compound of formula II wherein $R^1$, $R^2$, $R^3$, and $R^4$ are as herein defined and $PG^1$ denotes a suitable protecting group,
  (a) after the protecting group has been cleaved,
  (b) is treated with a reducing agent, and
  (c) is treated with an oxidising agent.

The invention thus relates to a process for preparing the compounds of formula I.

The invention further relates to a process for preparing a compound of formula II, by reacting a compound of formula III,

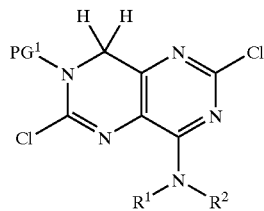

(III)

wherein $R^1$, $R^2$ and $PG^1$ are as herein defined, with an amine of formula IV, $$R^3R^4NH \qquad (IV)$$

wherein $R^3$ and $R^4$ are as herein defined,
optionally in the presence of a base.

The invention further relates to a process for preparing a compound of formula III, wherein a compound of formula V,

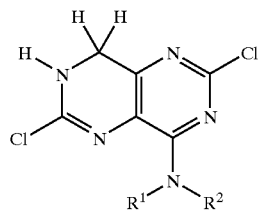

(V)

wherein $R^1$ and $R^2$ are as herein defined, is provided with a suitable protecting group ($PG^1$).

The invention also relates to a process for preparing the compounds of formula V by reducing a compound of formula VI,

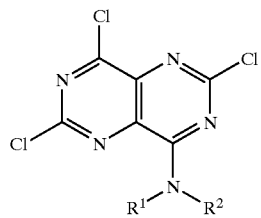

(VI)

wherein $R^1$ and $R^2$ are as herein defined; and a process for preparing a compound of formula VI by reacting 2,4,6,8-tetrachloropyrimido[5,4-d]pyrimidine with an amine of formula VIII, $$R^1R^2NH \qquad (VIII)$$

wherein $R^1$ and $R^2$ are as herein defined.

The invention further relates to the new intermediate products of formulae II, III, V and VI.

The term "alkyl" as used hereinbefore and hereinafter with respect to the groups $R^1$, $R^3$ and/or $R^4$ denotes a straight-chain or branched alkyl group having up to 6 C-atoms, preferably 1 to 4 C-atoms. Methyl, ethyl, n-propyl, i-propyl, n-butyl and tert-butyl are particularly preferred.

The term "alkenyl" as used hereinbefore and hereinafter with respect to the group $R^4$ denotes a straight-chain or branched alkenyl group having up to 6 C-atoms, preferably 3 to 5 C-atoms. Allyl, but-2-enyl, but-3-enyl, pent-2-enyl, pent-3-enyl and pent-4-enyl are particularly preferred.

The term "aryl" as used hereinbefore and hereinafter with respect to the group $R^2$ denotes an aromatic hydrocarbon group with 6 to 10 C-atoms, and aryl preferably denotes phenyl or naphthyl.

The term "suitable protecting group" as used hereinbefore and hereinafter with respect to the group $PG^1$ denotes a group familiar to those skilled in the art, e.g. a protecting group for amino groups as described in "Protective Groups in Organic Chemistry", edited by J. F. W. McOmie (Plenum Press), which is easily introduced, is inert to the subsequent reactions and can easily be cleaved again. Preferred protecting groups are the acetyl, trifluoroacetyl, benzoyl, ethoxycarbonyl, tert-butoxycarbonyl, benzyloxycarbonyl, benzyl, methoxybenzyl, mesyl, tosyl or 2,4-dimethoxybenzyl group.

A protecting group used is cleaved hydrolytically, for example in an aqueous solvent, e.g. in water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide or by ether splitting, e.g. in the presence of iodotrimethylsilane, at temperatures between 0 and 100° C., preferably at temperatures between 10 and 50° C.

A benzyl, methoxybenzyl or benzyloxycarbonyl is preferably cleaved by hydrogenolysis, e.g. with hydrogen in the presence of a catalyst such as palladium/charcoal in a solvent such as methanol, ethanol, ethyl acetate, dimethylformamide, dimethylformamide/acetone or glacial acetic acid optionally with the addition of an acid such as hydrochloric acid at temperatures between 0 and 50° C., but preferably at ambient temperature, and at a hydrogen pressure of 1 to 7 bar, preferably from 3 to 5 bar.

A methoxybenzyl group can also be cleaved in the presence of an oxidising agent such as cerium(IV)ammonium nitrate in a solvent such as methylene chloride, acetonitrile or acetonitrile/water at temperatures between 0 and 50° C., but preferably at ambient temperature. However, a 2,4-dimethoxybenzyl group is preferably cleaved in trifluoroacetic acid in the presence of anisol. A tert-butyloxycarbonyl group is preferably cleaved by treating with an acid such as trifluoroacetic acid or hydrochloric acid, optionally using a solvent such as methylene chloride, dioxane or ether.

The term "heterocyclyl group" as used hereinbefore and hereinafter with respect to the group $R^3$ or the group formed by $R^3$ and $R^4$ with the enclosed nitrogen atom denotes a saturated or unsaturated 4- to 7-membered, nitrogen-containing heterocyclyl group which may optionally contain, in addition to carbon atoms and at least one nitrogen atom, other heteroatoms selected from among oxygen and sulphur. The following heterocyclyl groups are preferred:

saturated 5- or 6-membered heterocyclyl groups which
contain one or two nitrogen atoms, particularly pyrrolidine, piperidyl and piperazyl, or
contain one nitrogen atom and an oxygen or sulphur atom, particularly morpholino and thiomorpholino.

If one of the groups $R^1$ to $R^4$ is referred to as an "optionally substituted" group, this group may have one or more substituents, preferably 1, 2 or 3, particularly 1 or 2 substituents. These substituents are groups which are inert under the reaction conditions of the process according to the invention and do not provoke any noticeable side reactions. Preferred substituents are selected from among fluorine, chlorine, bromine, carboxy, carboxy-$C_{1-3}$-alkyl, carboxy-$C_{1-3}$-alkoxy, alkoxycarbonyl-$C_{1-3}$-alkoxy, cyano, trifluoromethoxy, trifluoromethyl, $C_{1-3}$-alkyl, hydroxy, $C_{1-3}$-alkoxy, thiol, $C_{1-3}$-alkylthio, phenyl-$C_{1-3}$-alkoxy, amino, amino-$C_{1-3}$-alkyl, $C_{1-3}$-alkylamino $C_{1-3}$-alkylamino-$C_{1-3}$-alkyl, di-($C_{1-3}$-alkyl)-amino and di-($C_{1-3}$-alkyl)-amino-$C_{1-3}$-alkyl.

In a preferred embodiment the groups $R^1$ to $R^4$ have the following meanings:

$R^1$ denotes hydrogen or methyl, particularly hydrogen, $R^2$ denotes phenyl which may be substituted by one or two halogen atoms, particularly fluorine and/or chlorine, particularly 3-chloro-4-fluorophenyl, $R^3$ denotes hydrogen or methyl, particularly hydrogen, and $R^4$ denotes a 5- or 6-membered, nitrogen-containing heterocycle which may be substituted by one or two $C_{1-3}$-alkyl groups, particularly 1-methylpiperid-4-yl, or $R^3$ and $R^4$ together with the enclosed nitrogen atom form a 5- or 6-membered, nitrogen-containing heterocycle which may be substituted by one or two groups selected from among amino, $C_{1-3}$-alkyl and di-($C_{1-3}$-alkyl)-amino-$C_{1-3}$-alkyl, particularly amino, methyl and diethylaminomethyl, most preferably 4-amino-4-methylpiperid-1-yl.

In a preferred embodiment of the process according to the invention for preparing the compound of formula I:

in step (b) the compound obtained after the protecting group has been cleaved is hydrogenated in the presence of a transition metal catalyst or with hydrogen iodide optionally in the presence of phosphorus;

in step (c) the compound obtained in step (b) is treated with a peroxodisulphate or hydrogen peroxide.

Stage II→I

Step (a)

The reaction of the compound of formula II, wherein $PG^1$ is a $C_{1-6}$ alkylcarbonyl group, with an aqueous base, preferably an alkali metal base such as lithium hydroxide, sodium hydroxide or potassium hydroxide, is generally carried out at a temperature of 0° C. to 150° C., preferably 10° C. to 100° C., particularly at about 40 to 80° C., optionally in the presence of an inert solvent, such as for example toluene or tetrahydrofuran and a protic solvent such as for example an alcohol or water or mixtures thereof. Preferably, 0.8 to 2, particularly 0.9 to 1.2 equivalents of the base are used to 1 equivalent of the compound of formula II.

In a particularly preferred embodiment about 0.9 to 1.1 equivalents of the sodium hydroxide in the form of an approximately 2 N aqueous solution are added at ambient temperature to a mixture of one equivalent of the compound of formula II and 5 to 20 parts methanol and 0.5 to 2 parts tetrahydrofuran (THF) based on 1 part compound of formula II and the mixture is heated to boiling for about 30 minutes to 2 hours. The mixture obtained is cooled and then further processed in the next step (b) without any other purification.

Step (b)

Dechlorination, Variant A:

The compound obtained after the protecting group has been cleaved is generally hydrogenated in the presence of a transition metal catalyst. The hydrogenation is generally carried out at a temperature of 20° C. to 150° C., preferably 40° C. to 120° C., particularly at the boiling temperature of the diluent, at a hydrogen pressure of about 1–120 bar, in the presence of an ether, such as for example diethylether, tert-butyl-methylether, dioxane or tetrahydrofuran, an alcohol, such as for example methanol, ethanol or isopropanol, a hydrocarbon, such as for example cyclohexane or n-hexane or mixtures thereof, particularly in the presence of the diluent obtained from step (a). Instead of the hydrogen formic acid may also be used as the hydrogen donor. In this case the reaction is generally carried out at normal pressure and 5 to 20 parts formic acid are used to 1 part of the catalyst. Preferably, 0.01 to 0.90, particularly 0.01 to 0.10 parts of a catalyst consisting of palladium and activated charcoal is used, containing 1 to 25%, preferably 5 to 15% palladium, to 1 part of the compound obtained after the protecting group has been cleaved. The hydrogenation is generally complete under the conditions described after 1 to 100 hours, preferably 10 to 80 hours. The crude product obtained is further processed in the next step after distillation of the solvent but no other purification.

In a particularly preferred embodiment the mixture obtained in step (a) is evaporated to dryness and the residue is taken up in THF and methanol. Pd/C (5–15%) is added and the mixture is refluxed. After the addition of 2 to 20 ml of formic acid, the mixture is stirred for 20 to 75 hours. It is left to cool to ambient temperature, filtered and evaporated to dryness. The residue is suspended in water and ethyl acetate, made weakly basic with a concentrated ammonia solution and stirred. The crystalline product is isolated, optionally recrystallised and dried.

Dechlorination, Variant B:

Alternatively, the compound obtained after the protecting group has been cleaved may be treated with hydrogen iodide, optionally in the presence of phosphorus. The reaction is generally carried out at a temperature of 20° C. to 150° C., preferably 40° C. to 120° C., particularly at the boiling temperature of the diluent, in the presence of a polar solvent, particularly a carboxylic acid, such as for example acetic acid or propionic acid, or an aqueous inorganic acid such as for example hydrochloric acid, hydrobromic acid, hydriodic acid or mixtures thereof or water. The reaction is generally carried out at normal pressure, preferably using 6 to 6.5 equivalents of hydrogen iodide in the form of a 30- to 60% aqueous solution based on 1 equivalent of the compound obtained after the protecting group has been cleaved. Preferably, the reaction is carried out in the presence of red phosphorus, using 1.0 to 3.0, preferably 1.8 to 2.5 equivalents phosphorus based on 1 equivalent of the compound obtained after the protecting group has been cleaved. The reaction is generally complete under the conditions specified after 0.5 to 10 hours, preferably 1 to 8 hours. The crude product obtained is further processed in the next step after distillation of the solvent but no other purification.

In a particularly preferred embodiment the mixture obtained in step (a) is evaporated down, taken up in glacial acetic acid and added dropwise to a suspension of red phosphorus in hydriodic acid (57%). The mixture is refluxed for 3 to 5 hours, decolorised and neutralised. The product is isolated and dried.

Step (c)

The compound obtained in step (b) is preferably oxidised in the presence of an aqueous acid with a peroxodisulphate or hydrogen peroxide. The oxidation is generally carried out at a temperature of 0° C. to 150° C., preferably 40° C. to 120° C., particularly at the boiling temperature of the diluent, in the presence of an acid, such as for example acetic acid, trifluoroacetic acid, hydrochloric acid, nitric acid, phosphoric acid or sulphuric acid or mixtures thereof, particularly in the presence of water. Preferably, 0.8 to 2.0, particularly 0.9 to 1.5 equivalents of the oxidising agent are used, particularly in the form of a 20 to 40% aqueous solution of hydrogen peroxide or a 20- to 50% aqueous solution of sodium peroxodisulphate based on one equivalent of the compound obtained in step (b). The oxidation is generally complete under the conditions specified after 10 minutes to 30 hours, preferably 15 minutes to 24 hours. The crude product obtained is further processed in the next step after distillation of the solvent but no other purification.

In a particularly preferred embodiment 1 equivalent of the compound obtained in step (b) is taken up in 5 to 15% sulphuric acid and at boiling temperature combined with 0.01 to 0.10 equivalents of potassium iodide and 1.0 to 2.0, preferably 1.2 to 1.5 equivalents of hydrogen peroxide in the form of a 35% solution. The mixture is stirred for 10 to 30 minutes and an aqueous solution of sodium bisulphite and ethanol is added. Then the mixture is allowed to cool slowly to ambient temperature and stirred. The product that crystallises out is filtered and dried.

In another particularly preferred embodiment 1 equivalent of the compound obtained in step (b) is taken up in a mixture of glacial acetic acid and water (20- to 40%) and combined with 1.0 to 2.0, preferably 1.1 to 1.6 equivalents of sodium peroxodisulphate in the form of an approximately 30 to 35% aqueous solution. The mixture is stirred for 30 to 300 minutes at a temperature of 20 to 75° C. The solid formed is filtered off, suspended in water, neutralised with concentrated ammonia solution and extracted with ethyl acetate. The organic phase is separated off, dried and evaporated down. The residue is taken up in ethanol and converted into the hydrochloride of the compound of formula I by the addition of ethanolic HCl. The crystallised product is filtered off and dried.

Stage III→II

In a preferred embodiment of the process according to the invention for preparing the compound of formula II:

the reaction is carried out in the presence of a tertiary amine;

the reaction is carried out in a temperature range of 0° C. to 150° C.

The reaction with the amine of formula IV is expediently carried out in a diluent such as methanol, ethanol, isopropanol, butanol, tetrahydrofuran, dioxane, toluene, chlorobenzene, dimethylformamide, dimethylsulphoxide, ethyleneglycolmonomethylether, ethylenglycoldiethylether or sulpholane or mixtures of these diluents, optionally in the presence of an inorganic base, e.g. sodium carbonate or potassium hydroxide, or a tertiary organic base, e.g. triethylamine, N-ethyl-diisopropylamine or pyridine, while the latter may simultaneously serve as solvent, and optionally in the presence of a reaction accelerator such as a copper salt, a corresponding amino-hydrohalide or alkali metal halide at temperatures between 0 and 150° C., but preferably at temperatures between 20 and 120° C. The reaction may however also be carried out without a solvent or in an excess of the compound of general formula IV used. The reaction is generally carried out at normal pressure, using 0.8 to 2.0, preferably 0.9 to 1.5, particularly 1.0 to 1.5 equivalents of a compound of formula IV based on 1 equivalent of the compound of formula III. The reaction is generally complete under the conditions specified after 15 to 600 minutes, preferably 30 to 180 minutes. The crude product obtained is generally purified by recrystallisation or may be further processed in the next step without any other purification.

In a particularly preferred embodiment 0.8 to 1.8, preferably 1.0 to 1.6 equivalents of the amine of formula IV, particularly 1-methyl-4-aminopiperidine or 4-methylpiperidin-4-ylamine, is added dropwise to a mixture of 1 equivalent of the compound of formula III, THF and/or methanol and optionally 1 to 2 equivalents of triethylamine at ambient temperature. The mixture is stirred for 10 to 90 minutes at 20 to 80° C. After cooling, water is added and the mixture is stirred. The product that crystallises out is filtered off, washed with water and dried. After recrystallisation from ethyl acetate it is filtered and dried.

Stage V→III

In a preferred embodiment of the process according to the invention for preparing the compound of formula III:

the compound of formula V is reacted with a $C_{1-6}$ carboxylic acid or a reactive derivative thereof in the presence of a base, preferably a $C_{1-6}$ carboxylic acid chloride in the presence of a tertiary amine, particularly acetyl chloride, in the presence of N-ethyldiisopropylamine.

The acylation is expediently carried out with a corresponding halide or anhydride in a solvent such as methylene chloride, chloroform, carbon tetrachloride, ether, tetrahydrofuran, ethyl acetate, dioxane, benzene, toluene, acetonitrile or sulpholane optionally in the presence of an inorganic or organic base, preferably a tertiary amine at temperatures of −20 to 150° C., preferably at temperatures from −10 to 120° C., particularly at ambient temperature. However, it may also be carried out with the free acid, optionally in the presence of an acid-activating agent or a dehydrating agent, e.g. in the presence of isobutyl chloroformate, thionylchloride, trimethylchlorosilane, hydrogen chloride, sulphuric acid, methanesulphonic acid, p-toluenesulphonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole, N,N'-carbonyldiimidazole or N,N'-thionyldiimidazole or triphenylphosphine/carbon tetrachloride, at temperatures between −20 and 200° C., but preferably at temperatures between −10 and 160° C. The reaction is generally carried out at normal pressure, using 0.8 to 2.0, preferably 0.9 to 1.5, particularly 1.0 to 1.5 equivalents of a carboxylic acid derivative, based on 1 equivalent of the compound of formula V. The reaction is generally complete under the conditions specified after 15 to 300 minutes, preferably 30 to 120 minutes. The crude product obtained is generally purified by recrystallisation or may be further processed in the next step without any other purification.

In a particularly preferred embodiment 1.1 to 1.5, particularly about 1.3 equivalents of acetylchloride are added dropwise to a mixture of 1 equivalent of formula V, N-ethyldiisopropylamine and ethyl acetate at 0 to 20° C. The mixture is stirred for 60 to 120 minutes at ambient temperature and washed with water at 40 to 90° C. The product is recrystallised from ethanol, filtered off and dried.

Stage VI→V

In a preferred embodiment of the process according to the invention for preparing the compound of formula V:

the compound of formula VI is reduced with a boranate, particularly with sodium boranate in the presence of a base and a polar solvent.

The reduciton may be carried out by catalytic hydrogenation with hydrogen in the presence of a catalyst such as palladium/charcoal or platinum in a solvent such as methanol, ethanol, ethyl acetate, dimethylformamide, dimethylformamide/acetone or glacial acetic acid, optionally with the addition of an acid such as hydrochloric acid at temperatures between 0 and 50° C., but preferably at ambient temperature, and at a hydrogen pressure of 1 to 7 bar, but preferably 3 to 5 bar.

Preferably, the reduction is carried out with a boranate selected from among lithium boranate, sodium boranate and potassium boranate, expediently in a diluent such as water, methanol, ethanol, isopropanol, butanol, tetrahydrofuran, dioxane, toluene, chlorobenzene, dimethylformamide, dimethylsulphoxide, ethyleneglycolmonomethylether, ethyleneglycoldiethylether or sulpholane or mixtures of these diluents, optionally in the presence of an inorganic base, e.g. sodium carbonate, sodium hydroxide or potassium hydroxide, or a tertiary organic base, e.g. triethylamine, N-ethyldiisopropylamine or pyridine, at temperatures of −20 to +60° C., preferably −10 to +20° C. The reaction is generally carried out at normal pressure using 0.9 to 4.0, preferably 1.1 to 1.9, more particularly 1.6 to 1.8 mol of a boranate, based on 1 mol of the compound of formula VI. The reaction is generally complete under the conditions specified after 15 to 600 minutes, preferably 60 to 240 minutes. The crude product obtained is generally purified by recrystallisation or may be further processed in the next step without any other purification.

In a particularly preferred embodiment a mixture of about 1.75 mol sodium borohydride, water and sodium hydroxide in the form of an approximately 2N sodium hydroxide solution is added dropwise to a mixture of 1 mol of a compound of formula VI and ethyl acetate at 0 to 5° C. The mixture is stirred for another 1 to 3 hours at 0 to 20° C. and then heated to 60 to 80° C. The suspension is filtered and cooled to about 0° C. The product that crystallises out is isolated and dried.

Tetrachlorohomopurine Stage→VI

The reaction with the amine of formula VII is expediently carried out in a diluent such as methanol, ethanol, isopropanol, butanol, tetrahydrofuran, dioxane, toluene, chlorobenzene, dimethylformamide, dimethylsulphoxide, ethyleneglycolmonomethylether, ethyleneglycoldiethylether, sulpholane or water or mixtures of these diluents, particularly THF, optionally in the presence of an inorganic base, e.g. sodium carbonate or potassium hydroxide, or a tertiary organic base, e.g. triethylamine, N-ethyldiisopropylamine or pyridine, at temperatures of 0 to 80° C., preferably 5 to 50° C., particularly 10 to 30° C. The reaction is generally carried out at normal pressure, using 0.7 to 1.2, preferably 0.8 to 1.0, particularly about 0.95 equivalents of a compound of formula VII based on 1 equivalent of water-dampened tetrachlorohomopurine. The reaction is generally complete under the conditions specified after 15 to 600 minutes, preferably 30 to 180 minutes. The crude product obtained is generally purified by recrystallisation or may be further processed in the next step without any other purification.

In a particularly preferred embodiment, a solution of 0.8 to 0.95 equivalents of the amine of formula VII, particularly 3-chloro-4-fluoraniline in THF, is added dropwise to a mixture of 1 equivalent of tetrachlorohomopurine and tetrahydrofuran at 10 to 20° C. The mixture is stirred for 10 to 50 minutes at ambient temperature, activated charcoal is added and stirring is continued for another 10 to 20 minutes at ambient temperature. Then the reaction mixture is filtered in water and the filter residue is washed with THF. The aqueous suspension is stirred at ambient temperature and the product is then isolated and dried.

A major advantage of the process according to the invention is that it enables the compounds of formula I to be produced on an industrial scale starting from an easily obtainable starting material, namely 2,4,6,8-tetrachloropyrimido[5,4-d]pyrimidine (tetrachlorohomopurine).

Other advantageous aspects of the method according to the invention are the high space/time yields of the present process and the high yield and purity of the associated intermediate products, which can be further processed without being purified by chromatography.

The Examples that follow serve to illustrate the processes carried out by way of example for preparing the compound of formula I. They are to be understood as being possible methods given solely as examples without restricting the invention to their content.

EXAMPLE 1

(3-chloro-4-fluorophenyl)-(2,6,8-trichloropyrimido [5,4-d]pyrimidin-4-yl)amine (1)

At 15° C. a solution of 72.78 g (0.5 mol) of 3-chloro-4-fluoroaniline in 200 ml of THF is added dropwise to a suspension of 269.3 g of water-dampened tetrachlorohomopurine (about 50%, corresponding to about 0.5 mol) in 1820 ml of tetrahydrofuran (THF). The mixture is stirred for 30 minutes at ambient temperature, 13.5 g of activated charcoal are added and stirring is continued for another 15 minutes at ambient temperature. Then the reaction mixture is filtered in 4.1 l of water and the filter residue is washed with 200 ml of THF. The aqueous suspension is stirred for 30 minutes at ambient temperature and the product is then filtered off and dried in vacuo. Yield: 189 g (99.7%, based on the aniline), melting point 229.6° C.

250 MHz-$^1$H-NMR (CDCl$_3$) (ppm)=8.83 br s, 1H, NH; 7.95 dd, 1H, aniline-H; 7.69 ddd, 1H, aniline-H; 7.19 dd, 1H, aniline-H.

EXAMPLE 2

(3-chloro-4-fluorophenyl)-(2,6-dichloro-7,8-dihydropyrimido[5,4-d]pyrimidin-4-yl)amine (2)

At 2° C. a solution of 191.99 g (5.079 mol) of sodium borohydride in 520 ml of water and 22 ml of 2N sodium hydroxide solution is added dropwise to a suspension of 1100 g (2.902 mol) of (1) in 22 l of ethyl acetate. The mixture is stirred for 2 hours at 10° C. and then heated to 71° C. The suspension is filtered through Celite and cooled to 0° C. The product that crystallises out is filtered off and dried at 40° C. until a constant weight is attained.
Yield: 957.1 g (95.2%). melting point: 227.4° C.

250-MHz-$^1$H-NMR (DMSO) (ppm)=9.15 br s, 1H, NH; 8.79 br s, 1H, NH; 8.00, dd, 1H, aniline-H; 7.73 ddd, 1H, aniline-H; 7.39 t, 1H, aniline-H; 4.55 s, 2H, CH$_2$.

EXAMPLE 3

1-[2,6-Dichloro-8-(3-chloro-4-fluorophenylamino)-4H-pyrimido[5,4-d]pyrimidin-3-yl]ethanone (3)

At 10° C., 56.4 ml (0.789 mol) of acetylchloride are added dropwise to a suspension of 210.6 g (0.608 mol) of (2) and 176 ml of N-ethyldiisopropylamine (0.95 mol) in 2.1 l of ethyl acetate. The mixture is stirred for 90 minutes at ambient temperature and then washed 3 times with 700 ml of water at 60° C. The organic phase is evaporated down and combined with 590 ml of ethanol. The mixture is briefly brought to boiling point, cooled to 0–5° C. and stirred at this temperature for 30 minutes. The product that crystallises out is filtered off and dried at 60° C. in vacuo. Yield: 180.3 g (76.3%), melting point: 177.6° C.

250 MHz-$^1$H-NMR (CDCl$_3$) (ppm)=7.80 dd, 1H, aniline-H; 7.70 s, 1H, NH; 7.55 ddd, 1H, aniline-H; 7.15 t, 1H, aniline-H; 4.89 s, 2H, CH$_2$; 2.51 s, 3H, CH$_3$.

EXAMPLE 4

1-[6-chloro-8-(3-chloro-4-fluorophenylamino)-2-(1-methylpiperidin-4-ylamino)-4H-pyrimido[5,4-d] pyrimidin-3-yl]ethanone (4)

47.2 g (0.413 mol) of 1-methyl-4-aminopiperidine is added dropwise at ambient temperature to a mixture of 123.3 g (0.317 mol) of (3), 740 ml of THF and 61.7 ml (0.445 mol) of triethylamine. The mixture is stirred for 30 min at 50° C. It is left to cool to 40° C., 1480 ml of water are added and the mixture is then stirred for 90 minutes at 10° C. The product that crystallises out is filtered off, washed with 150 ml of water and dried in vacuo at 60° C. The product is dissolved in 1150 ml of ethyl acetate at boiling temperature. It is cooled to 10° C., filtered and the product that crystallises out is dried at 60° C. in vacuo.
Yield: 128.9 g (87.2%).

250-MHz-$^1$H-NMR (CDCl$_3$) (ppm)=8.70 br s, 1H, NH; 7.80 dd, 1H, aniline-H; 7.72 s, 1H, NH; 7.50 ddd, 1H, aniline-H; 7.13 t, 1H, aniline-H; 4.75 s, 2H, CH$_2$; 4.03–3.87 CH$_2$CHNCH$_2$; 2.82–2.65 m, 2H, CH$_2$CH$_2$N; 2.38 s, 3H, CH$_3$; 2.33 s, 3H, CH$_3$; 2.33–2.19 m, 2H, CH$_2$CH$_2$N; 2.18–2.02 m, 2H, CHCH$_2$CH$_2$; 1.75–1.60 m, 2H, CHCH$_2$CH$_2$.

EXAMPLE 5

8-(3-chloro-4-fluorophenylamino)-2-(1-methylpiperidin-4-ylamino)pyrimido[5,4-d] pyrimidine (5)

9 ml of 2N sodium hydroxide solution are added to a mixture of 9 g (0.019 mol) of (4), 81 ml of methanol and 9 ml of THF and the mixture is refluxed for 1 hour. Then 0.45 g of Pd/C (10%) are added and 4.5 ml of formic acid are added dropwise at boiling temperature. The mixture is refluxed for 24 hours, filtered off and evaporated down in vacuo to leave a residue. This is taken up in 90 ml of water and 7.2 ml of conc. hydrobromic acid and combined at ambient temperature with 3.9 ml of hydrogen peroxide (30%). The mixture is stirred for 5 hours at ambient temperature, then the product that crystallises out is filtered off and washed with water. The filter residue is dissolved in methanol, the free base is precipitated by the addition of 30 ml of water and 2N sodium hydroxide solution. Yield: 4.95 g (66%)

EXAMPLE 6

[6-(4-amino-4-methylpiperidin-1-yl)-2-chloro-7,8-dihydropyrimido[5,4-d]pyrimidin-4-yl]-(3-chloro-4-fluorophenyl)amine (6)

At 60° C. a mixture of 30.8 g (0.270 mol) of 4-methylpiperidin-4-ylamine and 100 ml of methanol is added dropwise to a suspension of 100 g (0.257 mol) of (3) in 690 ml of methanol. The mixture is stirred for 1 hour at 60° C., allowed to cool to 40° C., 280 ml of 2N sodium hydroxide solution are added and the resulting mixture is stirred for 3 hours at 60° C. Then 300 ml of methanol are distilled off and 600 ml of water are added. The mixture is stirred for 5 minutes at ambient temperature, filtered off and the residue is washed with 250 ml of water, 3 times 50 ml of acetone and 100 ml of methyl-tert-butylether and dried at 40° C. in vacuo. Yield: 100.5 g (92.2%), melting point 211.5° C. 400 MHz-$^1$H-NMR (DMSO) (ppm)=8.55 br s, 1H, NH; 8.05 dd, 1H, aniline-H; 7.78 ddd, 1H, aniline-H; 7.47 t, 1H, aniline-H; 6.90 br s, 1H, NH; 4.28 s, 2H, CH$_2$; 3.68 m, 2H, CH$_2$; 3.45 m, 2H, CH$_2$, 3.32 br s, 2H, NH$_2$; 1.37 m, 4H, 2CH$_2$; 1.05 s, 3H, CH$_3$.

EXAMPLE 7

[6-(4-amino-4-methylpiperidin-1-yl)-4-(3-chloro-4-fluorophenylamino)-pyrimido[5,4-d]pyrimidine (7)

Dechlorination:

A mixture of 80 g (0.182 mol) of (6) in 160 ml glacial acetic acid at 90° C. is added dropwise to a suspension of 11.7 g (0.378 mol) of red phosphorus in 150 ml of hydriodic acid (57%, 1.134 mol). The mixture is refluxed for 4 hours, 5 g of activated charcoal are added, the mixture is then filtered and the residue is washed with glacial acetic acid and water. The filtrate is added dropwise, with vigorous stirring, to a solution of 270 ml water, 270 ml of methanol and 270 ml of sodium hydroxide solution (50%). The mixture is stirred for a further 30 minutes at 15° C. and the solid precipitated is filtered off. This is washed twice with 500 ml of water, then suspended in 500 ml of water, filtered off and dried in vacuo at 45° C. Yield: 65.2 g (91.9%)

Oxidation, Variant A:

0.35 g (0.002 mol) of potassium iodide and 10.9 ml (0.112 mol) of 35% hydrogen peroxide are added at boiling temperature to a solution of 34 g (0.084 mol) of the dechlorinated compound in 500 ml of water and 38.7 ml of concentrated sulphuric acid. The mixture is stirred for 20 minutes, a solution of 7 g of sodium bisulphite in 10 ml of water and 150 ml of ethanol are added thereto. The mixture is then left to cool slowly to ambient temperature and stirred for another 3 hours. The product that crystallises out is filtered off and dried in vacuo at 40° C. Yield 34.3 g (84.1%) in the form of the sulphate. A suspension of 42 g of the sulphate in 600 ml of water and 40 ml of concentrated ammonia solution is extracted with 1.5 l of ethyl acetate. The combined organic phases are washed with water, dried with sodium sulphate and evaporated down in vacuo until crystallisation begins. The mixture is stirred for 2 hours at 0° C., the product that crystallises out is filtered off and dried in vacuo. Yield: 25.5 g (76.6%).

Oxidation, Variant B:

A solution of 8.9 g (0.037 mol) of sodium peroxodisulphate in 25 ml of water is added dropwise at ambient temperature to a solution of 10 g (0.025 mol) of the dechlorinated compound in 100 ml of water and 5.7 ml of glacial acetic acid. The mixture is stirred for 30 minutes at 60° C. and overnight at ambient temperature. Then 200 ml of ethyl acetate and 30 ml of concentrated ammonia solution are added. The phases are separated, the aqueous phase is extracted with 100 ml of ethyl acetate and the combined organic phases are evaporated to dryness. The residue is taken up in 140 ml of ethyl acetate at boiling temperature, then 80 ml of ethyl acetate are distilled off and the residue is cooled to 0° C. The product that crystallises out is filtered off and dried in vacuo. Yield: 6.2 g (63.9%).

What is claimed is:

1. A process for preparing a 4,6-diaminopyrimido[5,4-d] pyrimidine of the formula I,

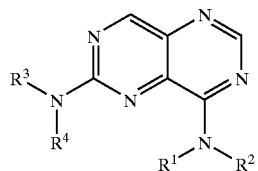

wherein
$R^1$ is a hydrogen atom or a $C_1$–$C_6$ alkyl group,
$R^2$ is an optionally substituted $C_6$–$C_{10}$ aryl group,
$R^3$ is a hydrogen atom or a $C_1$–$C_6$ alkyl group, and
$R^4$ is a hydrogen atom or an optionally substituted $C_1$–$C_6$ alkyl, $C_3$–$C_6$ alkenyl, $C_3$–$C_8$ cycloalkyl or a 4- to 7-membered, nitrogen-containing heterocycle group, or
$R^3$ and $R^4$ together with the nitrogen atom linked to them are an optionally substituted saturated 5- or 6-membered nitrogen-containing heterocyclic group containing one or two nitrogen atoms or one nitrogen atom and one oxygen or sulfur atom,
which process comprises the following steps:
(a) treating a compound of formula II,

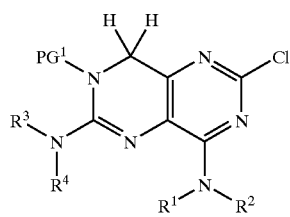

wherein $R^1$, $R^2$, $R^3$, and $R^4$ are as herein defined and
$PG^1$ is a suitable protecting group, so as to cleave the protecting group,
(b) treating the deprotected species formed by the preceding step with a reducing agent, to form a reduced intermediate, and
(c) treating the reduced intermediate with an oxidising agent, to form the compound of the formula I.

2. The process according to claim 1, wherein the protecting group is a $C_{1-6}$ alkylcarbonyl group and it is cleaved by treating with an aqueous base.

3. The process according to claim 1, wherein in step (b) the compound obtained after the protecting group has been cleaved is hydrogenated in the presence of a transition metal catalyst or treated with hydrogen iodide, optionally in the presence of phosphorus.

4. The process according to claim 1, wherein in step (c) the compound obtained in step (b) is treated with a peroxodisulphate or hydrogen peroxide.

5. A process according to claim 1, wherein
$R^1$ hydrogen or methyl,
$R^2$ represents phenyl, which may be substituted by one or two halogen atoms,
$R^3$ hydrogen or methyl,
$R^4$ represents a 5- or 6-membered nitrogen containing heterocycle, which may be substituted by one or two $C_{1-3}$ alkyl groups, or
$R^3$ and $R^4$ together with the nitrogen atom linked to them represent a substituted saturated 5- or 6-membered nitrogen-containing heterocyclic group, which may be substituted by one or two groups selected from amino, $C_{1-3}$ alkyl and di($C_{1-3}$ alkyl)-amino-$C_{1-3}$ alkyl.

6. A process according to claim 2, wherein in step (a) the compound of formula II is treated with an aqueous base at a temperature of 0° C. to 150° C. in the presence of an inert solvent.

7. A process according to claim 3, wherein in step (b) the hydrogenation is carried out at a temperature of 20° C. to 150° C., at a hydrogen pressure of 1–120 bar, in the presence of an ether, an alcohol, an hydrocarbon or a mixture thereof.

8. A process according to claim 4, wherein step (c) is carried out at a temperature of 0° C. to 150° C. in the presence of an acid.

9. A process for preparing a 4,6-diaminopyrimido[5,4-d] pyrimidine of the formula I,

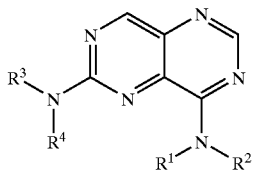

(I)

wherein
$R^1$ is a hydrogen atom or a $C_1$–$C_6$ alkyl group,
$R^2$ is an optionally substituted $C_6$–$C_{10}$ aryl group,
$R^3$ is a hydrogen atom or a $C_1$–$C_6$ alkyl group, and
$R^4$ is a hydrogen atom or an optionally substituted $C_1$–$C_6$ alkyl, $C_3$–$C_6$ alkenyl, $C_3$–$C_8$ cycloalkyl or a 4- to 7-membered, nitrogen-containing heterocycle group, or $R^3$ and $R^4$ together with the nitrogen atom linked to them are an optionally substituted saturated 5- or 6-membered nitrogen-containing heterocyclic group containing one or two nitrogen atoms or one nitrogen atom and one oxygen or sulfur atom, which process comprises the following steps:
(a) treating a compound of formula II,

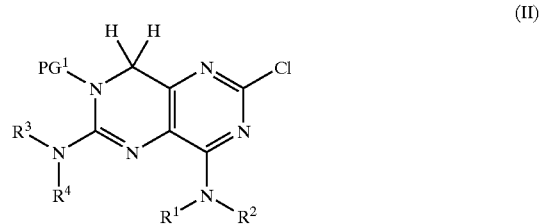

(II)

wherein $R^1$, $R^2$, $R^3$, and $R^4$ are as herein defined and wherein $PG^1$ is a $C_{1-6}$ alkylcarbonyl group, with an aqueous base, to cleave the group $PG^1$, (b) reducing the species formed by the preceding step, either by hydrogenation in the presence of a transition metal catalyst or by treatment with hydrogen iodide, to form a reduced intermediate, and (c) treating the reduced intermediate of the preceding step with an aqueous acid with a peroxodisulphate or hydrogen peroxide, to form the compound of the formula I.

* * * * *